United States Patent [19]

Knapp et al.

[11] Patent Number: 4,479,905

[45] Date of Patent: Oct. 30, 1984

[54] NITRATION PROCESS

[75] Inventors: Gordon G. Knapp; Marguerite S. Baylerian; Paul D. Seemuth, all of Baton Rouge, La.

[73] Assignee: Ethyl Corporation, Richmond, Va.

[21] Appl. No.: 533,223

[22] Filed: Sep. 19, 1983

[51] Int. Cl.³ .............................................. C07C 77/02
[52] U.S. Cl. ........................................ 260/467; 44/57
[58] Field of Search .............................. 44/57; 260/467

[56] References Cited

U.S. PATENT DOCUMENTS 4,251,455 2/1981 Gebauer ............................... 260/467
4,417,903 11/1983 Hinkamp .......................... 260/467 X

FOREIGN PATENT DOCUMENTS 837044 6/1960 United Kingdom ................ 260/467

Primary Examiner—Leland A. Sebastian
Attorney, Agent, or Firm—Donald L. Johnson; John F. Sieberth; Joseph D. Odenweller

[57] ABSTRACT

A mixture of aliphatic primary monohydric alcohol and alkoxyalkanol is continuously nitrated by reaction with a nitric-sulfuric acid mixture at −10° to 15° C. to yield an organic nitrate mixture containing substantial amounts of alkoxyalkyl nitrate useful as a cetane improver in diesel fuel.

10 Claims, No Drawings

NITRATION PROCESS

BACKGROUND

To some extent cetane improvers have been used for many years to increase the cetane number of diesel fuels. Higher cetane value leads to faster engine start especially in cold weather, quieter engine operation, less smoke and possibly less injector coking. Recently use of cetane improvers has greatly increased due to increased demand for diesel fuel and the lower natural cetane number of diesel base stocks caused by more severe refining of crude oil to make unleaded gasoline of acceptable octane number.

Presently the most common cetane improvers are primary alkyl nitrates such as amyl nitrate, hexyl nitrate, octyl nitrate and the like. These can be readily made by reacting a primary alcohol with a mixture of nitric and sulfuric acid. It is known that the cetane increase in most diesel fuels caused by alkoxyalkyl nitrates is much greater on a weight basis than that available from a primary alkyl nitrate. However, alkoxyalkyl nitrates are very difficult to make by the common commercial process of reacting an alcohol with a mixed nitric-sulfuric acid. It is possible to conduct such a nitration of an alkoxy-alcohol as a batch operation at low temperature over a short reaction period. If the reaction period extends over about 5-10 minutes the reaction temperature becomes uncontrollable and violently erupts spewing the entire reaction mixture out of the reaction vessel. This is referred to as a fume-off.

It has been attempted by us to avoid this fume-off problem by conducting the nitration on a continuous basis by feeding the alkoxyalcohol and mixed nitric-sulfuric acid continuously to a reaction vessel and withdrawing reaction mixture such that the average residence time in the reaction vessel is short enough such that the reaction would have been successful as a batch operation. However after a period of time oxidation products begin to build-up in the reaction vessel leading to an increase in decomposition rate and eventually to the same uncontrollable fume-off.

Accordingly, a need exists for a process capable of making alkoxyalkyl nitrates on a continuous basis while avoiding violent and possibly dangerous fume-offs.

SUMMARY

It has now been discovered that an organic nitrate mixture containing substantial amounts of alkoxyalkyl nitrate can be made using conventional continuous nitration equipment and a mixed nitric-sulfuric acid nitrating agent by utilizing an alcohol feed mixture which contains up to about 50 weight percent of an alkoxyalcohol and using a defined nitric-sulfuric acid mixture and feed ratio.

DESCRIPTION OF THE PREFERRED EMBODIMENTS

A preferred embodiment of this invention is a continuous process for making an organic nitrate mixture containing a substantial amount of an alkoxyalkyl nitrate, said process comprising:

(A) forming an alcohol mixture of (i) about 50-95 wt % of a primary alcohol containing 4 to about 12 carbon atoms and (ii) about 5-50 wt % of an alkoxyalkanol having the structure

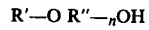

wherein R' is an alkyl group containing 1-12 carbon atoms, R" is a divalent aliphatic hydrocarbon group containing 2-4 carbon atoms and n is an integer from 1-4.

(B) forming an acid mixture consisting essentially of about 10-25 weight percent $HNO_3$ and 50-75 weight percent $H_2SO_4$, the balance being water.

(C) concurrently feeding said alcohol mixture and said acid mixture to a reaction zone forming a nitration mixture, said feeding being at a ratio such that (i) the moles of $HNO_3$ is at least 1.05 times the combined moles of said primary alcohol and said alkoxyalcohol in said alcohol mixture fed to said reaction zone and (ii) the moles of $H_2SO_4$ is at least 0.55 times the total moles of water, said primary alcohol and said alkoxyalcohol in the combined alcohol mixture—acid mixture feed, said feeding being at a rate which provides an average residence time in said reaction zone of about 3-10 minutes, said nitration mixture being maintained at a temperature of about $-10°$ C. to $15°$ C.

(D) removing said nitration mixture from said reaction zone at a rate which maintains a substantially constant nitration mixture volume in said reaction zone.

(E) separating an organic nitrate mixture from said nitration mixture containing a substantial amount of an alkoxyalkyl nitrate.

The alcohol mixtures used in the process can contain about 50-95 weight percent of an aliphatic monohydric primary alcohol having about 4-12 carbon atoms. Examples of such alcohols are n-butanol, isobutanol, n-pentanol, 2-methyl butanol, 3-methyl butanol, n-hexanol, 2-methyl pentanol, 3-methyl pentanol, 2-ethyl butanol, n-octanol, 2-ethyl hexanol, 3-ethyl hexanol, n-decanol, 2-ethyl octanol, n-dodecanol, 2-ethyl decanol and the like including mixtures thereof.

More preferred primary alcohols are those containing about 5-10 carbon atoms such as mixed primary amyl alcohols, n-hexanol, 2-ethyl butanol, n-octanol, 2-ethyl hexanol, n-decanol, 2-ethyl octanol and the like including mixtures thereof.

The most preferred alcohols are the primary octanols such as 2-ethyl hexanol.

The alkoxyalkanols have the structure

wherein R' is an alkyl group containing 1-12 carbon atoms, R" is a divalent aliphatic hydrocarbon group containing 2-4 carbon atoms and n is an integer from 1-4 including mixtures of such alkoxyalkanols. They are readily made by reacting $C_{2-4}$ alkylene oxides with $C_{1-12}$ alcohols. Typical alkoxyalkanols are 2-methoxy ethanol, 2-ethoxy-1-propanol, 2-decyloxy-1-butanol and the like. The most preferred alkoxyalkanol is 2-ethoxy ethanol.

The alcohol mixtures can contain up to about 50 weight percent alkoxyalkanol. Amounts greater than this will lead to a fume-off in continuous operation. Although there is no real minimum it is preferred to use at least 5 weight percent alkoxyalkanol in order to obtain a measurable benefit from the greater cetane increasing property of the alkoxyalkyl nitrates.

Preferably the alcohol mixture contains about 10 to 40 weight percent alkoxyalkanol. More preferably the alcohol mixture contains about 20-35 weight percent alkoxyalkanol and the balance is $C_{4-12}$ primary aliphatic alcohol.

A highly preferred alcohol mixture is about 30 weight percent 2-ethoxyethanol and 70 weight percent 2-ethyl hexanol.

The nitrating acid mixture consists essentially of nitric acid, sulfuric acid and water. A useful mixed acid can contain about 10-25 weight percent $HNO_3$, 50-75 weight percent $H_2SO_4$ and the balance, if any, water. A more preferred acid mixture consists essentially of about 15-25 weight percent $HNO_3$, 60-75 weight percent $H_2SO_4$ and the balance, if any, water. Excellent results have been achieved with a mixed acid consisting of 18-22 weight percent $HNO_3$, 65-70 weight percent $H_2SO_4$ and the balance water.

The nitric-sulfuric nitrating acid mixture should contain an amount of $H_2SO_4$ such that the spent acid after nitration contains less than 2 moles of water per mole of $H_2SO_4$. In the nitration reaction each mole of alcohol and alkoxy alkanol will produce one mole of water. Accordingly the moles of $H_2SO_4$ used in the nitration should be at least 0.5 times the total of the moles of water in the initial mixed nitric-sulfuric acid plus the moles of primary alcohol and alkoxyalkanol.

In a more preferred embodiment the moles of $H_2So_4$ fed to this nitration reaction in a given time should be at least 0.55 and still more preferably at least 0.6 times the total of the moles of water in the mixed acid feed plus the moles primary alcohol and alkoxyalkanol fed in the same time.

In addition to the above limitation a further requirement is that the amount of $HNO_3$ in the mixed acid fed in a given time be at least 1.05 times the combined moles of primary alcohol and alkoxyalkanol fed to the reaction during the same given time. More preferably the moles of $HNO_3$ feed is about 1.1-1.3 times the moles of primary alcohol plus alkoxyalkanol feed.

The continuous reaction is carried out by concurrently feeding the alcohol mixture and the mixed nitric-sulfuric acid to a reaction zone in a ratio which satisfies the above limitations as to $H_2SO_4$ ratio and $HNO_3$ ratio. The continuous reaction can be started by first filling the reaction zone with an acid mixture which corresponds with a typical spent acid composition—that is the composition of the acid mixture after the nitration. This is about 75-80 weight percent $H_2SO_4$, about 4 weight percent $HNO_3$ and about 16-21 weight percent water. The nitration mixture in the reaction zone is maintained at about $-15°$ C. to $20°$ C. during the nitration process by cooling. A preferred temperature range is about $-10°$ C. up to $15°$ C.

The nitration mixture should be vigorously mixed during the nitration process. As a safety precaution it is recommended that means be provided to rapidly quench the nitration mixture in water if it becomes uncontrollable for any reason such as a break-down in the cooling system.

The total volume of acid mixture and alcohol mixture and the volume of the reaction zone control the average residence time. For example if the total volume of mixed acid and alcohol mixture fed every 5 minutes equals the volume of the reaction zone, then the average residence time is 5 minutes. A useful residence time range is about 1-15 minutes. A more preferred range is about 3-10 minutes and a still more preferred range is about 5-7 minutes. Best results are obtained using an average residence time as short as possible while still completing the nitration reaction. As a rule at higher operating temperatures a shorter residence time is required. For example, a residence time of 15 minutes might be satisfactory at $-10°$ C. whereas at $15°$ C. a residence time of 3 minutes might be required.

Nitration mixture is removed from the reaction zone at a rate which maintains a substantially constant volume. This is readily accomplished by providing an overflow discharge conduit. The overflow nitration mixture is then separated into a spent acid phase and an organic nitrate phase. This separation generally occurs spontaneously with the organic phase separating to the top. Under some circumstances it might be necessary to add water to the discharged nitration mixture to cause the organic nitrate phase to sink depending upon the specific gravity of the spent acid relative to the organic nitrate mixture. This water dilution also stabilizes the spent mixed acid.

The organic nitrate mixture contains a substantial amount of an alkoxyalkyl nitrate that could not be made using a continuous nitric-sulfuric process prior to the present invention. The amount of alkoxyalkyl nitrate varies with the concentration of alkoxyalkanol in the alcohol mixture feed.

The organic nitrate mixture is preferably washed to remove residual acid and other impurities. This is preferably carried out with an aqueous solution of sodium hydroxide or sodium carbonate. Good results can be achieved with about a 5-20 weight percent sodium hydroxide solution.

The washed neutralized organic nitrate mixture is then dried. This can be carried out by contacting the wet organic nitrate mixture with a desiccant such as calcined alumina.

The following examples illustrate how the process can be carried out.

EXAMPLE 1

An acid mixture was prepared consisting of 20 weight percent $HNO_3$, 68 weight percent $H_2SO_4$ and 12 weight percent water. The nitration reactor was an open 100 ml beaker having a side discharge conduit giving a working volume below the discharge of about 82 ml. The reactor was fitted with a high speed stirrer, a thermometer and cooling means. The reactor was first filled to the discharge conduit with 25 ml of synthetic spent acid (77 wt % $H_2SO_4$ - 4 wt % $HNO_3$) and 50 ml organic nitrates (30 wt % 2-ethoxyethyl nitrate and 70 wt % 2-ethyl hexyl nitrate). The stirrer was started and the mixture was cooled to $10°$ C.

Mixed acid feed was started at a rate of 8.2 ml/min and mixed alcohol feed (28.8 wt % 2-ethoxy ethanol, 72.2 wt % 2-ethyl hexanol) was started at a rate of 5.4 ml/min using metering pumps. This gave an average residence time of 6 minutes. Overflow through the discharge conduit was mixed with ice and allowed to separate and the top organic layer was removed, washed with aqueous sodium hydroxide and dried over Mg $So_4$.

The resultant product analyzed by NMR 25.2 weight percent 2-ethoxy ethyl nitrate and 74.2 weight percent 2-ethyl hexyl nitrate and was a very effective cetane increasing additive for diesel fuel.

EXAMPLE 2

Following the above general procedure an alcohol mixture consisting of 28 wt % 2-butoxyethanol and 72 wt % 2-ethyl hexanol was made. This was pumped into the continuous reactor with the same mixed acid at a ratio and rate to provide 1.1 moles of HNO₃ per mole of 2-butoxyethanol and 2-ethyl hexanol and an average 6 minutes residence time. Nitration temperature was maintained at 10° C. Product was recovered as in Example 1 and analyzed 30 weight percent 2-butoxyethyl nitrate and 70 weight percent 2-ethyl hexyl nitrate. It was an effective cetane improver in diesel fuel.

Only a small amount of the organic nitrate mixture need be added to diesel fuel to obtain a significant gain in cetane number. A useful concentration in petroleum diesel fuel is about 0.05 to about 5 wt %, more preferably about 0.1-0.5 wt %.

Recently alcohols have been used experimentally as diesel fuels. Alcohols require a much higher concentration of cetane improver. A useful concentration is about 3-20 wt %.

We claim:

1. Continuous process for making an organic nitrate mixture containing a substantial amount of an alkoxyalkyl nitrate, said process comprising:
   (A) forming an alcohol mixture of (i) about 50-95 wt % of a primary alcohol containing 4 to about 12 carbon atoms and (ii) about 5-50 wt % of an alkoxyalkanol having the structure

wherein R' is an alkyl group containing 1-12 carbon atoms, R'' is a divalent aliphatic hydrocarbon group containing 2-4 carbon atoms and n is an integer from 1-4;
   (B) forming an acid mixture consisting essentially of about 10-25 weight percent HNO₃ and 50-75 weight percent H₂SO₄, the balance being water;
   (C) concurrently feeding said alcohol mixture and said acid mixture to a reaction zone forming a nitration mixture, said feeding being at a ratio such that (i) the moles of HNO₃ is at least 1.05 times the combined moles of said primary alcohol and said alkoxyalcohol in said alcohol mixture fed to said reaction zone and (ii) the moles of H₂SO₄ is at least 0.55 times the total moles of water, said primary alcohol and said alkoxyalcohol in the combined alcohol mixture—acid mixture feed, said feeding being at a rate which provides an average residence time in said reaction zone of about 3-10 minutes, said nitration mixture being maintained at a temperature of about −10° C. to 15° C.;
   (D) removing said nitration mixture from said reaction zone at a rate which maintains a substantially constant nitration mixture volume in said reaction zone;
   (E) separating an organic nitrate mixture from said organic nitrate mixture containing a substantial amount of an alkoxyalkyl nitrate.

2. A process of claim 1 wherein R'' is the group —CH₂CH₂—.

3. A process of claim 2 wherein n is 1.

4. A process of claim 3 wherein R' contains 2-4 carbon atoms.

5. A process of claim 4 wherein said acid mixture consists essentially of about 15-25 weight percent HNO₃ and 60-75 weight percent H₂SO₄.

6. A process of claim 5 wherein said ratio of said mixture to said alcohol mixture is such that 1.1-1.5 moles of HNO₃ are fed to said reaction zone for each mole of the total primary alcohol and alkoxyalcohol feed.

7. A process of claim 6 wherein said primary alcohol contains 5-10 carbon atoms.

8. A process of claim 7 wherein said alkoxyalkanol is 2-ethoxy ethanol.

9. A process of claim 8 wherein said alcohol mixture consists essentially of about 20-40 weight percent 2-ethoxy ethanol.

10. A process of claim 9 wherein said acid mixture is about 18-22 weight percent HNO₃ and 65-70 weight percent H₂SO₄.

* * * * *